United States Patent [19]

Schlager

[11] Patent Number: 4,795,750
[45] Date of Patent: Jan. 3, 1989

[54] QUINAZOLINE COMPOUNDS

[75] Inventor: Ludwig H. Schlager, Nottebohmstrasse, Austria

[73] Assignee: Gerot-Pharmazeutika Gesellschaft, Vienna, Austria

[21] Appl. No.: 937,863

[22] Filed: Dec. 4, 1986

[30] Foreign Application Priority Data

Dec. 4, 1985 [AT] Austria ................... 3522/85

[51] Int. Cl.$^4$ ............... A61K 31/505; C07D 403/04; C07D 403/14
[52] U.S. Cl. ..................... 514/260; 544/284; 544/291
[58] Field of Search ............... 544/284, 291; 514/260

[56] References Cited

U.S. PATENT DOCUMENTS

| 4,138,561 | 2/1979 | Crenshaw et al. | 544/291 |
| 4,237,138 | 12/1980 | Campbell et al. | 544/291 |
| 4,271,300 | 6/1981 | Honkanen et al. | 544/291 |
| 4,377,581 | 3/1983 | Hess et al. | 544/284 |

OTHER PUBLICATIONS

Philippe, et al., "Chemical Abstracts," vol. 92, 1980, Col. 92:94422p.
Yasunobu, et al., "Chemical Abstracts," vol. 96, 1982, Col. 96:35297m.
Millen, et al., "Chemical Abstracts," vol. 10,2, Col. 102:17423n.

Primary Examiner—Glennon H. Hollrah
Assistant Examiner—James H. Turnipseed

[57] ABSTRACT

Quinazoline compounds of the general formula (I):

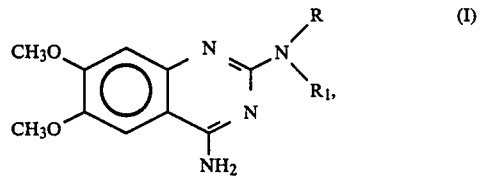

in which
(a) R is a hydrogen atom and $R_1$ is an -(2-pyrrolidinon-1-yl)-alkyl group,
(b) R is a methyl group and $R_1$ is an -(mono- or dialkoxyphenyl)-alkyl group,
(c) R together with $R_1$ forms a piperidine ring substituted with 2-keto-1-benzimidazolinyl radical in the 4-position of the piperidine group ring; or
(d) R together with $R_1$ forms a piperazine ring substituted with a hydroxyacyl group in the 4-position of the piperazine ring.

3 Claims, No Drawings

QUINAZOLINE COMPOUNDS

FIELD OF THE INVENTION

The present invention relates to quinazoline compounds useful as antihypertensive agents.

BACKGROUND OF THE INVENTION

A number of antihypertensive quinazoline derivatives is known which, although corresponding to general formula (I) defined below, have different substituents for R and $R_1$. Some of these active substances are used in therapy as α-blockers (see Drugs of Today 18, 552 (1982), and Drugs of The Future 9, 41–55 (1984)).

SUMMARY OF THE INVENTION

The present invention in one embodiment provides quinazoline compounds of the general formula (I)

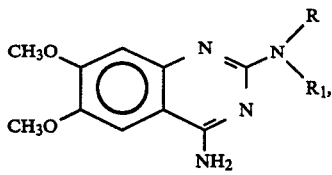

in which
(a) R is a hydrogen atom and $R_1$ is an ω-(2-pyrrolidinon-1-yl)-alkyl group,
(b) R is a methyl group and $R_1$ is an ω-(mono- or dialkoxy-phenyl)-alkyl group,
(c) R together with $R_1$ forms a piperidine ring substituted with a 2-keto-1-benzimidazolinyl radical in the 4-position of the piperidine ring; or
(d) R together with $R_1$ forms a piperazine ring substituted with a hydroxyacyl group in the 4-position of the piperazine ring.

The invention in another embodiment provides a process for preparing the compounds of formula (I). This process comprises reacting a 2-substitued 4-amino-6,7-dimethoxy-quinazoline of the general formula (II)

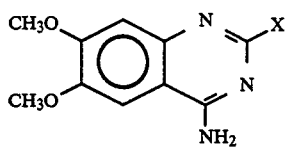

in which X is a functional group separable in the form of HX, such as a halogen atom or a sulfonyloxy group, preferably in an inert solvent or mixture of solvents such as alcohols, dioxane, dimethylformamide as well as the amine (III) mentioned below itself, and optionally in the presence of a phase transfer catalyst e.g. quaternary ammonium and phosphonium salts, with an amine of the general formula (III)

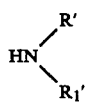

in which R' and $R_1'$ are as defined for R and $R_1$ above or in which R' and $R_1'$ combine and form an unsubstituted piperazine ring, preferably at a temperature of 50° to 160° C., the molar ratio of (II) to (III) being 1:1 to more than 1:100 (if (III) is used as solvent) and the ratio of phase transfer catalyst to compound (II) being about 0.01:1 to 1:1, which, after reaction with the compound of formula (II), is converted into a 4-(hydroxyacyl)-1-piperazinyl derivative by further reaction with a lactone e.g. β-butyrolactone, γ-butyrolactone, γ-valerolactone, δ-valerolactone, preferably at a temperature of 50° to 160° C., and, if desired, conversion of the derivatives of formula (I) obtained into salts by reaction with physiologically acceptable acids, e.g. HCl, $H_2SO_4$, tartaric acid, citric acid, methanesulfonic acid.

DETAILED DESCRIPTION OF THE INVENTION

The quinazoline derivatives of general formula (I) of the invention have antihypertensive activity. Compared with the prior art compounds, some of them show both α- and β-adrenolytic activity, are soluble in water even in the free base form and have a particularly low toxicity as well as a long-lasting effect.

The quinazolines of the general formula (II) used as starting compounds in the process of the present invention are known compounds (as disclosed in J. Chem. Soc. 1948, 1759; J. Med. Chem. 20, 148 (1977)) or may be prepared in a manner known per se. The same applies to the amine compounds of general formula (III).

The compounds of the invention may be administered alone or in association with pharmaceutically acceptable carriers to achieve effects against hypertension. Suitable carriers are e.g. lactose, starch, water, alcohols, liquid and solid polyethylene glycols.

The galenic processing to give tablets, capsules, solutions, suspensions or suppositories is performed in each case in a suitable manner using pharmaceutically acceptable carriers, diluents and adjuvants well known to one skilled in the art.

For lowering the blood pressure of hypertensive individuals, the dosage will be appropriately selected based on the specific blood pressure involved and the treatment is generally commenced with small doses. Generally, 1 to 100 mg of the active substance of the general formula (I) per day will be sufficient per application for an adult (70 kg).

The invention is now described in greater detail with reference to the following specific examples. Unless otherwise indicated herein, all parts, percents, ratios and the like are by weight.

EXAMPLE 1

A mixture of 2 g of 2-chloro-4-amino-6,7-dimethoxy quinazoline and 2 g of triethylbenzyl ammonium chloride was heated in 20 mls of amyl alcohol with stirring until the mixture boiled and 3 mls of N-(3-aminopropyl)-2-pyrrolidinone (Chem. Ber. 99, 2012 (1966)) were added thereto dropwise over a 5 hour period. After a reaction time of 15 hours, 1.5 mls of the pyrrolidinone base additionally were dropped thereinto and heated, until a sample on thin layer chromatography (Kieselgel 60 F 254, eluent: ethylacetate/methanol/2N ammonia=25:8:3) indicated the reaction was complete.

The mixture, after being concentrated on a rotary evaporator, was filtered and the precipitate was washed with isopropanol (1.4 g of crude product). The filtrate was evaporated to dryness, the residue was taken up into water and chloroform, the chloroform phase was extracted with 1N HCl, the hydrochloric phase was neutralized and extracted again with chloroform. After drying this chloroform solution with Na₂SO₄ (sicc.) an evaporation residue was obtained which was crystallized by triturating with isopropanol. This crude product was dissolved together with that obtained above in methanol and converted into the hydrochloride of 2-[3-(2-pyrrolidinon-1-yl)-propylamino]-4-amino-6,7-dimethoxy quinazoline by addition of alcoholic HCl. The product melted at 268°–271° C. (dec.).

EXAMPLE 2

A mixture of 5 g of 2-chloro-4-amino-6,7-dimethoxy quinazoline, 30 g of N-methyl-homoveratryl amine (Lloydia 33, 15–18) and 1 g of triethylbenzyl ammonium chloride was heated with stirring to 110° C. over a 3 hour period. Then the excess of N-methyl-homoveratryl amine was distilled off in vacuo. On standing in the cold, a precipitate was formed from the solution of the evaporation residue in acetone. After filtration with activated charcoal, the precipitate was recrystallized from methanol. The N-methyl-N-(4-amino-6,7-dimethoxy-quinazolin-2-yl)-homoveratryl amine hydrochloride obtained melted at 265°–270° C. with decomposition.

EXAMPLE 3

A suspension of 4.9 g of 2-chloro-4-amino-6,7-dimethoxy quinazoline in a solution of 4.87 g of 4-(2-keto-1-benzimidazolinyl)-piperidine (commercial product) in 150 ml of N-butanol was stirred at reflux until a clear solution was obtained, from which a precipitate was formed, and a sample indicated on thin layer chromatography (Kieselgel 60 F 254, eluent: ethyl acetate/methanol/2N ammonia=25:8:3) that the reaction was complete.

Acetone was added to the mixture after it has been concentrated on a rotary evaporator. The precipitated hydrochloride of 2-[4-(2-keto-1-benzimidazolinyl)-piperidino]-4-amino-6,7-dimethoxy quinazoline was recrystallized from methanol with filtration with activated charcoal. After decomposition commencing at 287° C., the product melted at 296°–298° C.

EXAMPLE 4

5 g of 2-piperazinyl-4-amino-6,7-dimethoxy quinazoline were heated in 15 g of γ-butyrolactone to 100° C. until a sample on thin layer chromatography (as described in Examples 1 and 3) indicated the reaction was complete. The precipitate formed overnight with cooling was removed and recrystallized from ethanol. The 1-(4-amino-6,7-dimethoxy quinazolin-2-yl)-4-(4-hydroxy-butyryl)-piperazine obtained showed a crystal transformation at 135°–140° C. and melted at 241°–243° C.

EXAMPLE 5

6 g of γ-butyrolactone were dropped slowly into a melt of 15 g of piperazine stirred at 120° C. Completion of reaction was indicated on thin layer chromatography (as described in Example 1) after treatment with iodine vapor. Excess piperazine was evaporated in vacuo and the remaining yellow oil was distilled at 48°–50° C./3 Torr. The 1-(4-hydroxybutyryl)-piperazine crystallized on standing and was reprecipitated from acetone/ethyl acetate, m.p. 99°–101° C.

1.8 g of this product together with 2.4 g of 2-chloro-4-amino-6,7-dimethoxy quinazoline in 20 mls of N-butanol were stirred at 100° C. After 4 hours the mixture was cooled and the precipitate obtained was removed. After recrystallization from methanol/ethyl acetate, the product described in Example 4 was obtained in the form of the hydrochloride thereof, m.p. 210°–215° C.

EXAMPLE 6

5 g of 2-piperazinyl-4-amino-6,7-dimethoxy quinazoline were heated in 15 g of β-butyrolactone at 100° C. over a 3 hour period. The cooled reaction mixture was diluted with ethyl acetate and the precipitate formed over night with cooling was removed. The mother liquor was extracted with 2N HCl, the acid extract was made alkaline with 50% NaOH and extracted several times with chloroform. The evaporation residue remaining after drying the chloroform solution and filtration thereof with activated charcoal together with the precipitate obtained already was recrystallized from ethyl acetate. The 1-(4-amino-6,7-dimethoxy quinazolin-2-yl)-4-(3-hydroxy-butyryl)-piperazine obtained melted at 220°–222° C.

EXAMPLE 7

15 mls of β-butyrolactone were dropped slowly into a melt of 25 g of piperazine stirred at 120° C. Then excess piperazine was evaporated in vacuo and the residue was distilled at about 60° C./4 Torr. The oil obtained consisted of 1-(3-hydroxybutyryl)-piperazine and had a refractive index $n_D^{25}$ of 1.5586.

1.8 g of this product were stirred with 2 g of 2-chloro-4-amino-6,7-dimethoxy quinazoline in 20 mls of n-butanol at 100° C. After 6 hours the mixture was cooled and the resulting precipitate was removed. The product was the hydrochloride of the product obtained according to Example 6, m.p. 281° C. (dec.).

The antihypertensive activity of the compound of Examples 6 and 7 has been studied in dogs. A distinct lowering of the blood pressure and an increase of the heart frequency have been observed. As further indication of the activation of the sympathetic system an increase of the plasma-renine-activity has been observed.

From the obtained results it can be concluded that the studied compound is active both by venous administration and by arterial administration.

According to the above-described procedures, additional compounds of the present invention were obtained as shown in the following table.

| Compounds of the General Formula (I) | | |
|---|---|---|
| $-N\begin{matrix}R\\ \\R_1\end{matrix}$ | base/salt | m.p. °C. |
| 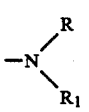 —N⌒N—CO.CHCH₃ <br>                     OH | hydrochloride | 230–232 |
| 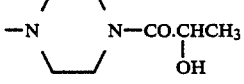 —N⌒N—CO.(CH₂)₄.OH | free base | 208–210 |
| 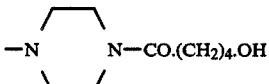 —N⌒N—CO.CH₂CH₂CHCH₃ <br>                         OH | free base | 233–235 |

| Compounds of the General Formula (I) | | |
|---|---|---|
| −N(R)(R₁) | base/salt | m.p. °C |
| −N(piperazine)N—CO.(CH₂)₅.OH | free base | 162–164 |
| −N(piperazine)N—CO.CH(OH)−phenyl | hydrochloride | 260–262 |

The mandelic piperazide [N-(2-hydroxy-2-phenylacetyl)-piperazine] used as an intermediate was obtained by heating the methyl ester of mandelic acid with excess piperazine to 120° C. After evaporation of the unreacted piperazine, an oil remained which was crystallized by triturating with isopropyl ether, m.p. 192° C.

While the invention has been described in detail and with reference to specific examples thereof, it will be apparent that changes and modifications can be made therein without departing from the spirit and scope thereof.

What is claimed is:

1. A quinazoline compound of the general formula (I)

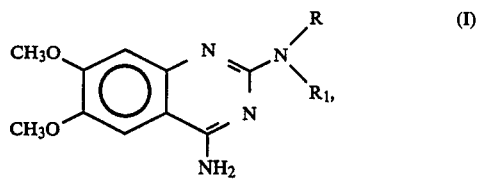

in which
 (a) R is a hydrogen atom and R₁ is an ω-(2-pyrrolidinon-1-yl)-alkyl group,
 (b) R is a methyl group and R₁ is an ω-(mono- or di-alkoxy-phenyl)-alkyl group.
 (c) R together with R₁ forms a piperidine ring substituted with a 2-keto-1-benzimidazolinyl radical in the 4-position of the piperidine ring; or
 (d) R together with R₁ forms a piperazine ring substituted with a hydroxyacyl radical in the 4-position of said piperazine ring, or a physiologically acceptable salt thereof.

2. A antihypertensive composition comprising a therapeutically effective amount of a quinazoline compound or the physiologically acceptable salt thereof as defined in claim 1 to lower the blood pressure and a pharmaceutically acceptable carrier or diluent.

3. A method of reducing the blood pressure of a subject comprising administering the antihypertensive composition according to claim 2 to said subject.

* * * * *